United States Patent

Trauth et al.

(10) Patent No.: US 8,207,382 B2
(45) Date of Patent: Jun. 26, 2012

(54) METHOD FOR ELIMINATING COLOR FORMING IMPURITIES FROM NITRO COMPOUNDS

(75) Inventors: Daniel M. Trauth, Crystal Lake, IL (US); Edward L. Little, Winfield, WV (US); Richard L. James, Eros, LA (US); John D. Gummere, Monroe, LA (US); Morteza Mokhtarzadeh, Charleston, WV (US); Li Wang, Arlington Heights, IL (US)

(73) Assignees: Dow Global Technologies LLC; ANGUS Chemical Company

( * ) Notice: Subject to any disclaimer, the term of this patent is extended or adjusted under 35 U.S.C. 154(b) by 49 days.

(21) Appl. No.: 12/934,803

(22) PCT Filed: Apr. 8, 2009

(86) PCT No.: PCT/US2009/039903
§ 371 (c)(1),
(2), (4) Date: Jan. 7, 2011

(87) PCT Pub. No.: WO2009/129098
PCT Pub. Date: Oct. 22, 2009

(65) Prior Publication Data
US 2011/0105806 A1   May 5, 2011

Related U.S. Application Data

(60) Provisional application No. 61/045,381, filed on Apr. 16, 2008.

(51) Int. Cl.
*C07C 27/26* (2006.01)
*C07C 205/00* (2006.01)

(52) U.S. Cl. ........................................ 568/958; 568/947

(58) Field of Classification Search .................. 568/947, 568/958
See application file for complete search history.

(56) References Cited

U.S. PATENT DOCUMENTS

| | | | |
|---|---|---|---|
| 2,229,532 A | 7/1937 | Vanderbilt et al. | |
| 2,267,309 A | 2/1940 | Senkus et al. | |
| 2,247,255 A | 6/1941 | Senkus | |
| 2,489,320 A | 11/1945 | Nygaard et al. | |
| 2,580,742 A | 1/1952 | Doumani et al. | |
| 2,597,753 A | 5/1952 | Schmitz et al. | |
| 2,739,174 A | 3/1956 | Ross | |
| 4,210,609 A | 7/1980 | Summers et al. | |
| 4,820,881 A | 4/1989 | Kupper | |

FOREIGN PATENT DOCUMENTS

WO   8502613 A1   6/1985

*Primary Examiner* — Jafar Parsa

(57) ABSTRACT

A method for stabilizing nitro compounds against discoloration. The method comprises reacting nitro compounds containing color-forming impurities with nitric acid, neutralizing and washing the product, and distilling therefrom purified nitro compounds.

10 Claims, No Drawings

METHOD FOR ELIMINATING COLOR FORMING IMPURITIES FROM NITRO COMPOUNDS

CROSS-REFERENCE TO RELATED APPLICATIONS

This is a §371 application of PCT International Patent Application No. PCT/US2009/039903 filed Apr. 8, 2009, and claims priority from U.S. Provisional Application No. 61/045,381, filed Apr. 16, 2008, each of which is incorporated herein by reference in its entirety.

FIELD OF THE INVENTION

The invention relates to a method for stabilizing nitro compounds against discoloration.

BACKGROUND OF THE INVENTION

Nitroparaffins are commercially produced by the vapor-phase nitration of hydrocarbon feedstock. The nitration generally produces a variety of products depending upon the reaction conditions and the feedstock structure. For instance, the commercial vapor phase process for propane nitration results in a mixture of four nitroparaffin products (nitromethane, 1-nitropropane, 2-nitropropane, and nitroethane) in essentially fixed relative concentrations.

Nitroparaffin products of the commercial vapor-phase nitration process are known to suffer from undesirable color formation during storage. To address this problem, the commercial process requires a chemical wash step prior to nitro compound distillation in order to eliminate color-forming impurities that cause discoloration. However, there are several disadvantages to current commercial processes, including the necessity, in some processes, for deepwell disposal of used wash solution. Another disadvantage is the tendency of commercial wash solutions to react with the nitroparaffins, resulting in a nitroparaffin yield loss. There is a need, therefore, for improved chemical wash processes.

BRIEF SUMMARY OF THE INVENTION

The invention provides a method for stabilizing liquid nitro compounds against discoloration. The method comprises: (a) reacting in a reactor a mixture comprising a liquid nitro compound containing color-forming impurities together with aqueous nitric acid, at a temperature of about 100 to 225 degrees centigrade and a pressure of about 150 and 1200 psi, wherein sufficient aqueous nitric acid is used to provide a nitric acid concentration of about 0.5 to 5 weight percent based on total weight of the mixture; (b) neutralizing the mixture (reactor effluent) of step (a) with a neutralizing agent and washing the neutralized mixture with water to remove residual salts; and (c) distilling the nitro compound from the mixture of step (b).

DETAILED DESCRIPTION OF THE INVENTION

As noted above, the invention provides a new method for the production of color stable nitro compounds, such as nitroparaffins, that have been prepared by a vapor-phase, or mixed vapor liquid-phase, nitration process. According to the invention, a heat treatment/oxidation method using a low level of nitric acid has been found to be effective at removing color-forming impurities in the nitro compounds. Without wishing to be bound by any particular theory, it is believed that color-forming impurities are unsaturated compounds, such as nitroolefins.

The method of the invention eliminates the environmental concerns of existing commercial wash processes. In particular, the aqueous neutralization solutions of the method of the invention are readily biotreated without the need for deepwell waste disposal. Further, little or no nitro compound losses occur during the heat treatment or neutralization step, thus mitigating yield reduction normally observed with commercial chemical wash processes.

The invention utilizes a heat treatment/oxidation process as the means by which impurities that impact eventual color stability, such as nitroolefins, are eliminated. More particularly, the method of the invention comprises: (a) reacting in a reactor a mixture comprising a liquid nitro compound containing color-forming impurities together with aqueous nitric acid, at a temperature of about 100 to 225 degrees centigrade and a pressure of about 150 and 1200 psi, wherein sufficient aqueous nitric acid is used to provide a nitric acid concentration of about 0.5 to 5 weight percent based on total weight of the reaction mixture; (b) neutralizing the mixture (i.e., reactor effluent) of step (a) with a neutralizing agent and washing the neutralized mixture with water to remove residual salts; and (c) distilling the nitro compound from the mixture of step (b).

Various steps of the method of the invention are carried out in a reactor which, at a minimum, is a vessel that is capable of being heated and pressurized. Advantageously, the reactor is made substantially of a corrosion resistant material, such as titanium. The reactor is optionally surrounded by a shell with input and output ports for feeding a heat transfer fluid to the outer surface of the reactor. The heat transfer fluid, which can be for example an oil, allows the temperature of the reaction to be controlled to within the desired parameters.

Typically, the reactor is of an elongated shape, such as a tube, that is positioned substantially vertically and in which the entry port is at or near one end of the reactor and the exit port at or near the other end, allowing the reactor to be operated in either upflow or downflow mode. When used in downflow mode, the reactor is positioned so that feed materials are added through an entry port at or near the top and then flowed down the reactor for sufficient residence time to allow reaction to occur. The product is then removed from an exit port at or near the bottom of the reactor. In upflow mode, feed materials are added at an entry port positioned at or near the bottom of the reactor, and product is collected at an exit port positioned at or near the top of reactor.

The reactor is optionally packed with a packing material to improve reactant mixing and heat transfer and/or to vary the reactor volume. Suitable packing materials include, for example, glass beads, random packing, or structured packing, such as those typically employed in distillation devices. Other packing materials are known in the art and may be used.

The nitro compound and nitric acid can be mixed, or partially mixed, prior to entry into the reactor or, alternatively, they can be added individually, with mixing to occur within the reactor. Further, the materials, whether added together or individually, can be individually or collectively pre-heated prior to entry into the reactor. In some preferred embodiments, the nitric acid and nitro compounds are pre-mixed and pre-heated to between about 160 and 180 degrees centigrade before introduction into the reactor.

The liquid nitro compound is preferably in the form of a product stream from a previously conducted nitration process. Nitration processes are well known in the art and include for example the vapor-phase nitration of hydrocarbons or aromatic compounds. In the invention, the product stream is preferably nitroparaffins. The nitroparaffin product stream can be prepared by the vapor phase nitration of a hydrocarbon, such as propane, in the presence of nitric acid at elevated temperature and pressure. The invention is applicable to other product streams, such as nitrated aromatics.

The nitric acid in the invention is delivered to the reactor in the form of an aqueous solution. Sufficient nitric acid is used such that the reaction mixture contains at least about 0.5 weight percent, preferably at least about 1 weight percent, of the acid based on the total weight of the material fed to the reactor. Further, the reaction mixture contains no more than about 5 weight percent, preferably no more than about 4 weight percent, and more preferably no more than about 3 weight percent, of the acid based on the total weight of the material fed to the reactor. In further embodiments, the nitric acid concentration is between about 1 and about 2 weight percent. The nitric acid weight percent can be calculated as follows: 100×nitric acid weight/(crude nitroparaffin stream weight+nitric acid weight+water diluent weight).

The reaction temperature within the reactor is generally controlled (for example with heat exchange fluid as described above) to at least about 100 degrees centigrade and to no more than about 225 degrees centigrade. In some embodiments, the temperature is at least about 125 degrees. In further embodiments, the temperature is no more than about 200 degrees. In other embodiments, the temperature is between about 150 and 200 degrees centigrade.

The pressure in the reactor should be maintained at least about 150 psi (10 atm), preferably at least about 250 psi (17 atm). Further preferably, the pressure is about 1200 psi (82 atm) or less, more preferably about 800 psi (41 atm) or less, further preferably about 500 psi (34 atm) or less. In further embodiments, the pressure is between about 300 psi (20 atm) and 500 psi (34 atm). Various methods known in the art can be used for maintaining the pressure within the desired range including, for example, through the use of a back-pressure regulator.

The residence time of the nitro compound and nitric acid reactants in the reactor is preferably at least about 30 seconds, more preferably at least about 60 seconds. Preferably, the residence time is 420 seconds or less, more preferably 300 seconds or less. In some embodiments, the residence time is between 120 seconds and 300 seconds. Residence time can be controlled in various ways including, for example, by the length and/or width of the reactor or through the use of packing material. Residence time is determined by dividing the volume of the reactor by the inlet flow rates.

Following sufficient residence time, the products are collected from the reactor through the reactor's exit port and subjected to a neutralization step. Typically, neutralization involves contacting the reactor products with a neutralizing agent, which can be a single agent or combination of agents, that will provide appreciable neutralizing capacity in the pH range of 7 to 9. A pH greater than 9 tends to increase the yield loss of the nitro compound, probably resulting from excessive conversion of nitro compounds to water soluble nitronate salts. Examples of suitable neutralizing agents include, without limitation, alkali metal carbonates, bicarbonates, and hydroxides. A preferred neutralizing agent is sodium bicarbonate. Amine-containing compounds that react with the nitro compounds are not favored for use in the invention. Alkali metal phosphates are generally ill-suited for conventional biotreatment, and are therefore also not favored.

The neutralizing agent is used in the form of a water based solution or dispersion, preferably at a concentration of between about 5 and about 10 weight percent, more preferably between about 6 and 9 weight percent. The ratio of nitro compounds from the reactor to the neutralizing agent is typically at least 3:1, preferably between about 5:1 and 8:1 by weight, but generally depends on the amount of residual acidity in the treated nitro compound. The wash temperature of the neutralizing step is preferably between about 40 and 60° C., more preferably between about 45 and 55° C.

Once the treated materials are neutralized, residual salts in the neutralized materials are removed and the distillation is completed. Salt removal and distillation can be conducted using techniques well known to those skilled in the art. As an example of salt removal, residual salts can be removed by a single wash or successive washes using water of suitable quality. For example of distillation, 2-nitropropane distills at about 80° C./200 mm Hg pressure. Nitromethane distills at about 62° C., nitroethane distills at about 72° C., and 1-nitropropane distills at about 90° C. (all at 200 mm Hg).

The following examples are illustrative of the invention but are not intended to limit its scope.

EXAMPLES

General. The reactor unit used in the following examples consists of two feed tanks and pumps, a shell-and-tube preheater/reactor, a shell-and-tube cooler, a back-pressure regulator, and two product collection vessels. All equipment exposed to reaction temperature is constructed of type 2 titanium tubing. A hot oil unit is used to heat and cool the preheater/reactor. The preheater/reactor dimensions are: 0.94 cm inner diameter by 0.76 to 0.97 meters long (2 different length reactors were used). A 0.32 cm outer diameter thermowell runs the length of the reactor down the centerline. Residence time is defined as the reactor volume divided by the flowrate of reactants fed to the reactor (at room temperature).

The reactor unit is of a continuous flow configuration. A typical experiment proceeds as follows: the hot oil unit is set to the desired temperature, reactants are charged to the feed tanks, and cooling water is turned on. Once the hot oil unit reaches its setpoint, the crude nitroparaffin pump is started. A visual inspection of the lines is made as the unit pressurizes to verify leak-free operation. The back-pressure regulator is adjusted to the desired operating pressure. The nitric acid feed is commenced following a second visual check. Reaction gases are piped through a flow meter then to the vent stack. Following a 30 to 45 minute line-out period, the product flow is switched to a clean product collector and the flowmeter totalizer is zeroed. A typical run lasts between 45 and 60 minutes depending on the flowrate (in order to collect an adequate size sample). Once the run is complete, the product is diverted to the line-out collection vessel, the hot oil unit and pumps are turned off, and the feed tanks are valved off. Cooling water is turned off approximately 30 minutes later after pumping has been stopped. Products are analyzed using routine gas chromatography techniques.

Example 1

Effect of Nitric Acid on Nitroolefin Elimination

Two experiments are completed at the following conditions: 200° C. hot oil, pressure of 1000 psig (68 atm), for a 3 minute residence time. In the first experiment, no nitric acid is used. Results show 37.0% 2-nitropropene and 2.2% 1-nitropropene elimination. In the second experiment, 1.5 weight % nitric acid is added to the crude nitroparaffins (weight percent of nitric acid is based on the total weight of materials fed to the reactor). Results show 94.6% 2-nitropropene and 85.5% 1-nitropropene elimination. This set of experiments clearly shows adding nitric acid improves the nitroolefin elimination.

Example 2

Effect of Temperature on Nitroolefin Elimination

Three experiments are completed at the following conditions: 1.5 weight % nitric acid added at a pressure of 300 psig (20.4 atm) for 3 minute residence time. In the first experiment, the hot oil is set at 125° C. Results show 69.8% 2-nitropropene and 56.3% 1-nitropropene elimination. In the second experiment, the hot oil is set at 175° C. Results show 96.2% 2-nitropropene and 87.8% 1-nitropropene elimination. In the third experiment, the hot oil is set at 200° C. Results show 98.1% 2-nitropropene and 96.3% 1-nitropropene elimination. This set of experiments shows the effectiveness of the process over a wide range of operating temperature. Nitroolefin removal is improved at 175-200° C. compared to the experiment at 125° C.

Example 3

Effect of Pressure on Nitroolefin Elimination

Two experiments are completed at the following conditions: 175° C. hot oil, 1.5 weight % nitric acid added and a 3 minute residence time. In the first experiment, the pressure is held at 150 psig (10.2 atm). Results show 96.2% 2-nitropropene and 75.3% 1-nitropropene elimination. In the second experiment, the pressure is held at 400 psig (27.2 atm). Results show 98.1% 2-nitropropene and 89.1% 1-nitropropene elimination.

Example 4

Effect of Residence Time on Nitroolefin Elimination

Two experiments are completed at the following conditions: 175° C. hot oil with 1.5 weight % nitric acid added, and pressure of 300 psig (20.4 atm). In the first experiment, the residence time is 1 minute. Results show 98.1% 2-nitropropene and 64.7% 1-nitropropene elimination. In the second experiment, the residence time is 3 minutes. Results show 96.2% 2-nitropropene and 87.8% 1-nitropropene elimination. Longer residence time improves the removal of 1-nitropropene.

Example 5

Washing and Distillation of Treated Crude Nitroparaffins

Treated crude nitroparaffin product is washed with 7.5% sodium bicarbonate solution at 120 F. (49° C.) and decanted to remove residual acid salts from the product. The neutralized crude nitroparaffin is washed and decanted three times with distilled water at 70 F. (21° C.).

The washed crude nitroparaffin product is distilled using a glass vigreux column (65 mm diameter×300 mm filling height) equipped with an electromagnetic distilling head. Pressure is maintained at 230 mm Hg. A 3:1 reflux ratio is used. Four fractions are collected as overhead product, with the first being a high water fraction followed by three relatively dry fractions with varying nitroparaffin composition.

The distilled nitroparaffin fractions are tested for color stability by various means and shown to exhibit stability attributes comparable to what is achieved using the commercial chemical wash processes.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A method for stabilizing liquid nitro compounds against discoloration, the method comprising:
   (a) reacting in a reactor a mixture comprising a liquid nitro compound containing color-forming impurities together with aqueous nitric acid, at a temperature of about 100 to 225 degrees centigrade and a pressure of about 150 and 1200 psi, wherein sufficient aqueous nitric acid is used to provide a nitric acid concentration of about 0.5 to 5 weight percent based on total weight of the mixture;
   (b) neutralizing the mixture of step (a) with a neutralizing agent and washing the neutralized mixture with water to remove residual salts; and
   (c) distilling the nitro compound from the mixture of step (b).

2. The method of claim 1 wherein the liquid nitro compound is mixed with the nitric acid prior to introduction into the reactor.

3. The method of claim 2 wherein the mixture of nitro compound and nitric acid is pre-heated to between about 160 and 180 degrees centigrade.

4. The method of claim 1 wherein the nitro compound is a nitroparaffin or mixture of nitroparaffins.

5. The method of claim 1 wherein the nitro compound is nitroparaffins selected from nitromethane, nitroethane, 1-nitropropane, 2-nitropropane and mixtures of two or more thereof.

6. The method of claim 1 wherein the nitro compound and nitric acid are reacted in the reactor for a residence time of at least about 30 seconds.

7. The method of claim 1 wherein the pressure is between about 300 psi and 500 psi.

8. The method of claim 1 wherein the temperature is between about 150 and 200 degrees centigrade.

9. The method of claim 1 wherein the neutralizing agent is selected from alkali metal carbonates, bicarbonates, hydroxides, and combinations of two or more thereof.

10. The method of claim 1 wherein the neutralizing agent is sodium bicarbonate.

* * * * *